(12) United States Patent
Cherfas et al.

(10) Patent No.: US 6,623,489 B2
(45) Date of Patent: Sep. 23, 2003

(54) DEVICE FOR DESTROYING FORMATIONS IN A BODY

(76) Inventors: Daniel Cherfas, 286 Corbin Pl. #5B, Brooklyn, NY (US) 11235; Marika Cherfas, 286 Corbin Pl. #5B, Brooklyn, NY (US) 11235; Michael Tsipov, 3026 Brighton 14th St., Brooklyn, NY (US) 11235

( * ) Notice: Subject to any disclaimer, the term of this patent is extended or adjusted under 35 U.S.C. 154(b) by 0 days.

(21) Appl. No.: 09/902,007

(22) Filed: Jul. 11, 2001

(65) Prior Publication Data
US 2003/0014058 A1 Jan. 16, 2003

(51) Int. Cl.[7] ................................................. A61D 1/12
(52) U.S. Cl. ....................................... 606/106; 606/159
(58) Field of Search ................................ 606/159, 157, 606/205, 210, 211, 106

(56) References Cited
U.S. PATENT DOCUMENTS 5,582,617 A * 12/1996 Klieman et al. ............ 606/170
5,667,472 A * 9/1997 Finn et al. .................. 600/104
5,782,834 A * 7/1998 Lucey et al. ................. 604/22
6,206,898 B1 * 3/2001 Honeycutt et al. .......... 606/159
6,398,798 B2 * 6/2002 Selmon et al. .............. 606/159

* cited by examiner

Primary Examiner—Kevin T. Truong
Assistant Examiner—Victor X Nguyen

(57) ABSTRACT

A device for destroying formations in a body has a tubular element introducible into a body to an area of a formation, a gripping element extended through the tubular element and having a front end provided with gripping means for grasping a formation, and a formation destroying element also extending through the tubular element and having a front end provided with a working part, the formation destroying element being rotatable so that during rotation of the formation destroying element with the working part the part in contact with the formation destroys the formation.

7 Claims, 3 Drawing Sheets

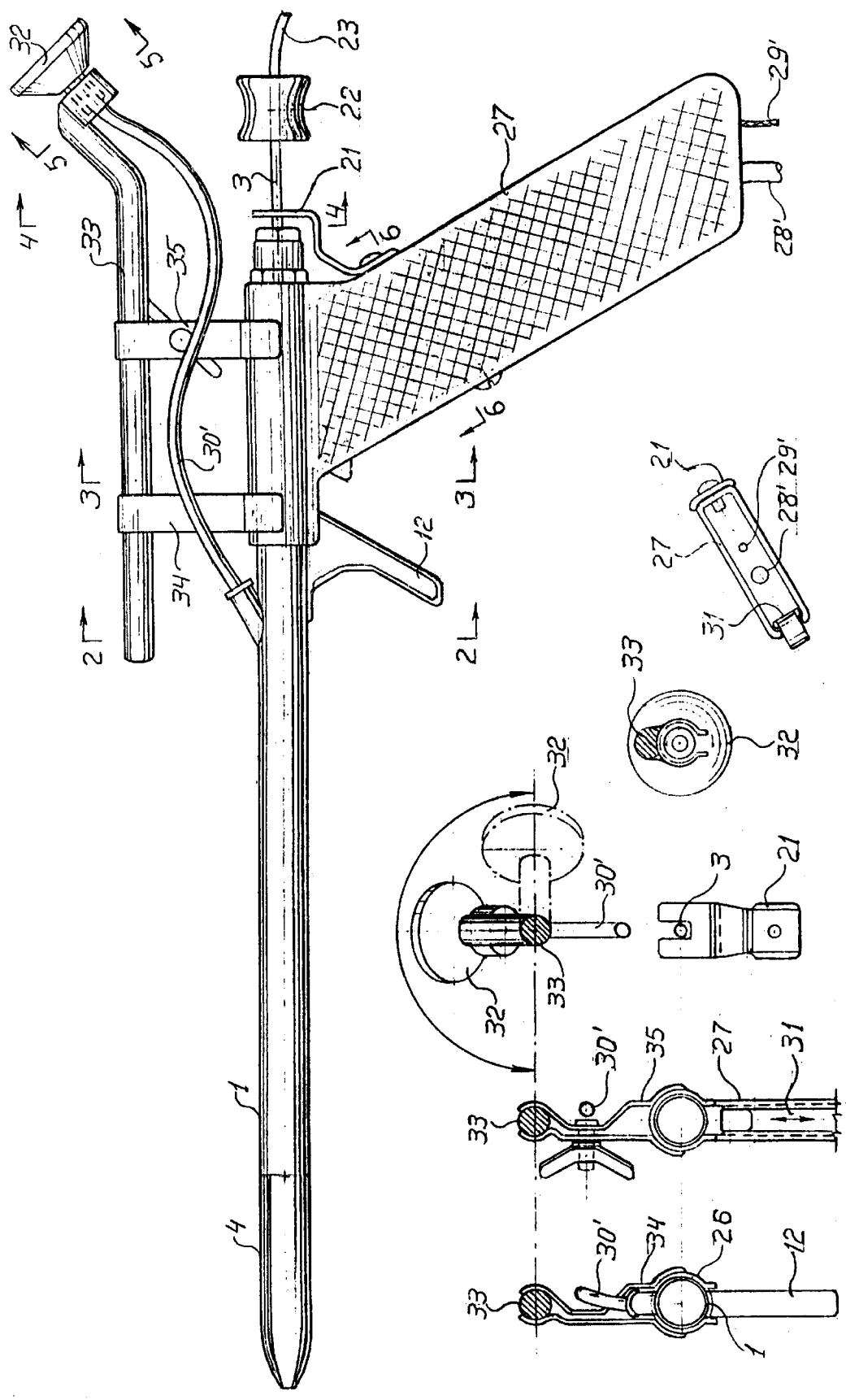

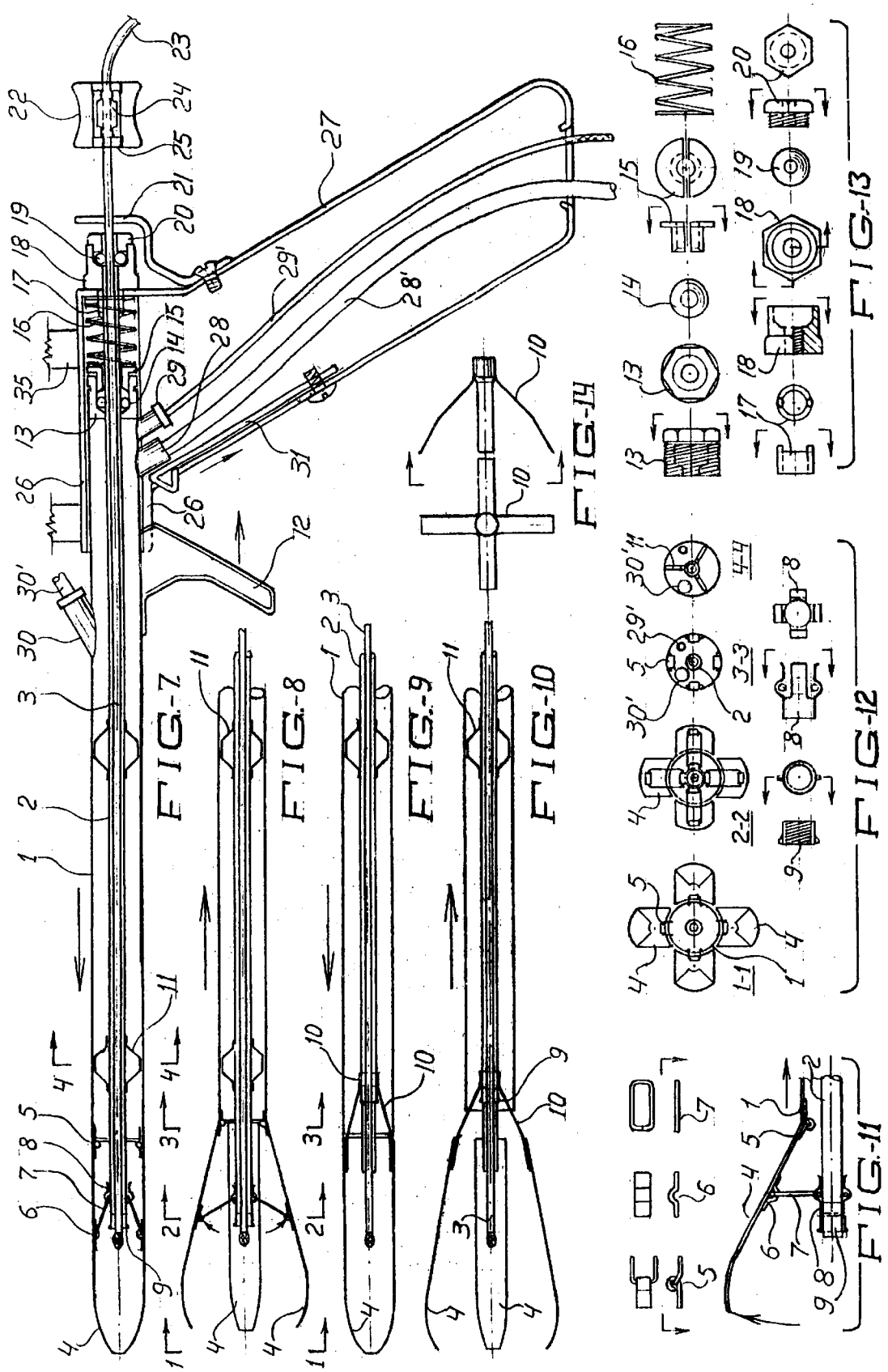

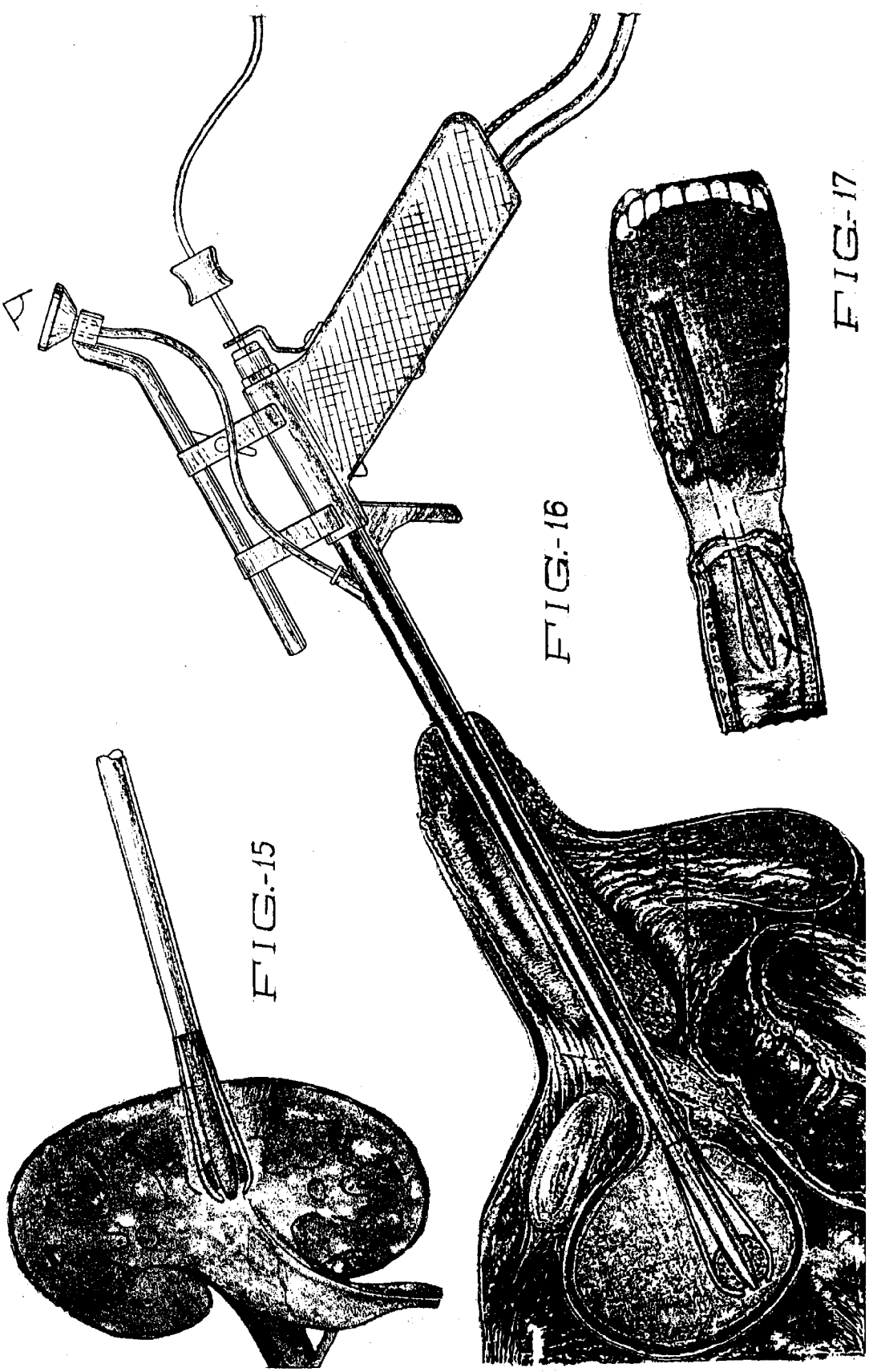

DEVICE FOR DESTROYING FORMATIONS IN A BODY

BACKGROUND OF THE INVENTION

The present invention relates to a device for destroying formations in a body, in particular in internal organs, in deep wounds and other areas which are difficult to access, without surgical operations, with minimal trauma, so that corresponding formations can be destroyed and if necessary extracted from the body. Foreign formation can include stones, growths, bullets logged in wounds, food stuck during eating, etc.

Devices for destroying corresponding formations in the body are known. Some of them include surgical devices with which a corresponding organ is made accessible by a surgical operation, and the formation is destroyed and/or removed. Other devices use for example ultrasound crashing of stones, etc. It is believed that existing devices can be further improved.

SUMMARY OF THE INVENTION

Accordingly, it is an object of the present invention to provide a device for destroying foreign formations in a body.

In keeping with these objects and with others which will become apparent hereinafter, one feature of present invention resides, briefly stated, in a device for destroying formations in a body, which includes a tubular member introducible into a body to an area of a foreign formation, a mechanical rotary tool introducible through said tubular member to the area of the foreign formation; and a working part provided on a distal end of said tool so that when said working head is introduced into contact with the formation and the tool is rotated, the formation is destroyed by the head of the tool.

When the device is designed in accordance with the present invention, it makes possible a destruction and if necessary withdrawal of formations from the body in a simple, efficient, and non intrusive way.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a general view of a device which uses a new method for destroying foreign formations in a body;

FIGS. 2, 3, 4, 5 and 6 are views showing a cross-section of the device shown in FIG. 1 taken along the lines 2—2, 3—3, 4—4, 5—5 and 6—6 correspondingly;

FIG. 7 is a view substantially corresponding to the view of FIG. 1 but showing a longitudinal cross-section of the device which uses a new method in accordance with the present invention;

FIG. 8 is a view showing one embodiment of the device of FIG. 1;

FIGS. 9 and 10 are views showing another embodiment of the device in accordance with the present invention in a closed and an open position correspondingly;

FIGS. 11 and 12 are views showing details of the inventive device of the embodiment of FIG. 8 in a front area;

FIGS. 13 is a view showing details of a rear area of the device which uses the inventive method;

FIG. 14 is a view showing a working head part of the device which uses the inventive method; and FIGS. 15, 16, and 17 are views showing the device which uses the inventive method used for destruction of formations in a kidney, in a male bladder and in a food pipe correspondingly.

DESCRIPTION OF THE PREFERRED EMBODIMENTS

A method of for destroying and/or extracting foreign formations in a body includes introduction of a tubular member which is identified as a whole with reference numeral 1. A tube 2 of a smaller diameter is located in the tubular member 1, and a rod 3 extends through an interior hollow of the tube 2. The rod 3 is a rigid shaft which has a front end provided with a working head, such as for example a drill, a bit, and the like. The opposite end of the rod 3 extends outwardly from the tubular member to be connected with a flexible shaft 23. The front, head part of the tubular member ends in cigar-shaped and composed of petal-shaped tongues 4. The tongues 4 have bent ends which form grippers when they are open.

In accordance with one embodiment of the present invention which involves the use of a hinges, each tongue is provided at its base with a hinge 5 for turning. The hinge 5 includes a plate which is bent from one side and in which a hook is introduced. The plate is soldered to the tongue and the hook is soldered to the inner surface of the end of the tubular member 1 as shown in FIGS. 7, 8, 11, 12. In order to control the turning, a hinge 6 is soldered or welded to an inner surface of each tongue at a distance from its axis of turning. The hinge 6 includes a bent plate 6 with a frame 7 in it. The central element of the hinge unit is a casing 8 which is composed of a spring, alloyed steel. Bent legs of the casing embrace the tube 2 from all sides. During mounting, second ends of the frames 7 are introduced into the hooks. The casing 8 is placed on the tube 2 and fixed from one side by a soldered abutments and from another side by a bush 9 which is screwed on the end of the pipe 2. In order to turn the bush, two abutments are soldered on its outer surface.

In accordance with another embodiment of the present invention, a gripper 10 composed for example of spring, alloyed steel, is arranged on the end of the pipe 2. The gripper which is fixed by the soldered abutments on the pipe 2 from one side is also locked by screwing of the bush 9 on the end of the pipe 2. Sliders 11 are soldered on the pipe 2 and form inner supports which fix the central position of the pipe 2 in the tubular member 1.

The rear end of the tubular member is shown in FIGS. 7 and 13. In order to provide hermetization of the tubular member a special bushing 13 is screwed into its rear part from outside. The bushing has a cavity, through which the pipe 2 extends. For hermetization of the pipe 2, a sealing ring 14 is arranged on it inside the bushing. Then halves of an insert 15 which is separated into halves is introduced into the interior of the bushing. The outer ends of the halves of the insert are supported on the inner side of the bushing and take a pressure from a spring 16. Furthermore, for fixing the tube 2 from a longitudinal and turning movement, a special bush 17 is placed on it and located in a chamber of the spring. The left side of the bush is soldered to the pipe 2. The right side of the bush is formed with two thorns which during mounting are inserted into the drilled openings in the rear wall of the upper part of the device. A special bushing 18 is screwed on the end of the pipe 2 which extends beyond the rear wall, and is tightened. The rigid shaft 13 extends through the bushing. For the hermetization in the bushing, a sealing ring 19 is provided. The interior of the bushing 18 is closed by a plug 20 which is screwed into it and the shaft 3 freely extends through the plug. The shaft 3 extends through a limiting member 21 which is screwed to the upper part of a handle of the device.

A control handle 22 formed as a coil is arranged at the outside, rear side of the device at a certain distance. An end of the rigid shaft 3 extends from the left side into the handle, while the end of the flexible shaft 23 which extends from a rotary drive is introduced from the right end. The ends of both shafts are arranged in known rolling or sliding bearings 25. Furthermore, the ends of both shafts are introduced into a connecting coupling 24. After the connection a coil 22 is placed on the bearings and the 20 coupling 24. After this, both outside races of the bearings are fixed in the coil.

The rear end of the tubular member and the spring are located in a cylindrical element 26 which embraces them but is open in the lower part. At the front, the open part of the cylindrical member has bend parts, in which an upper part of a cock 12 can move. The rear part of the open end of the cylindrical member transits into a hollow handle of the device 27. Two nipples 28 and 29 are soldered into the lower part of the tubular member. They are used for connection of a hose 28' for supply a cleaning medium, for example water. A nipple 29 is used for introducing an electric cable 29' for power supply to an illuminating bulb at the end of a light guide 30'. The hose and the electrical cable are extended from the device through a lower part of the handle so as not to interfere with one another and lead to a power source.

A window which is closed by a special cover 31 is located in the upper front part of the device handle. The cover has a triple function. From the outer side, its upper bend is a limiting member for the cock 12 when it is moved rearwardly. From the inner side, the upper part of the cover blocks the spring-biased tubular member and is a support for the nipple 28 in the tubular member. For disassembly of the device, the clamping screw is released and the cover is lowered so that the tubular member with the nipples can be removed and withdrawn from the window in the handle (hose 28' and cable 29').

The device can have a support for an eyepiece 32 and a light guide 30' which extends from the eyepiece and has a known construction. The light guide is inserted into the tubular member through a nipple 30. The eyepiece is arranged on a standing part of a member 33. The member 33 is movable and can move forwardly and rearwardly and turn to the left and right due to its circular cross-section. This member is arranged on two supports 34 and 35 which are soldered to the casing 26. The support 35 has a tightening nut for fixing the member with the eyepiece at any lower position.

The central rod 3 or the shaft can have any length. It can be exchangeable. It can have a head with any working elements, attachments, etc.

The device operates in the following manner.

A medical practitioner holds the device by taking its handle with all fingers of left or right hand. The tubular element is introduced into an interior organ or cavity of a patient. With monitoring of the movement of the tubular member on a screen or an X-ray device, the practitioner displaces the tubular element to a formation, for example a stone which has to be removed. With the pointing finger the practitioner pulls the cock 12, the cock presses the spring 16, so that the tubular member is moved rearwardly a few millimeters. In the embodiment with the hinge, the tubular element moves the tongues 4, the tongues 4 pull the frames 7 in which they are hingedly connected to them, and the frames 7 which have a hinged, immovable support on the tube 2 turn to the sides and move tongues outwardly. In the gripper embodiment, the tubular member gripper moves rearwardly and releases the spring biased elements of the gripper and they turn the tongues 4, so that the spaced tongues form gripping elements. The device with the tubular element is moved forwardly, and the tongues are placed on the formation, for example on a stone. The cock is then released forwardly, and the tubular member moved forwardly. In the hinged embodiment, the tongues which are pushed by the tubular element turn the frames 7, and the latter are turned in the hinges of the casing 8 so as to press the tongues to the center. In the gripper embodiment, the gripping tongues which are pushed by the tubular member also will press the tongues to the center so as to form gripping members which block the stone.

Then a not shown rotary drive is energized, and the rigid drill shaft 3 is rotated together with the working head formed for example as a tool. The practitioner looks into the eyepiece and sees the stone. By displacement of the coil 22 forwardly, the practitioner introduces the drill into the stone and causes its destruction. The removal of the destroyed stone does not cause any problem.

When the device is utilized in therapeutic purposes, the end of the shaft 23 can be provided with special attachments which are located in the front area of the tubular element when it is introduced into an organ. Then the front part is opened and the shaft of the attachment is moved forwardly for treatment of corresponding problems or for administration of medications. The head of the light guide can be also moved forwardly. For this purpose, the sealing cover is released on the nipple 30 and the light guide is moved and lengthened.

With the present device it is possible to spread tissues in order to perform examination and touch an object which has to be destroyed, removed or treated. It is possible to destroy and remove foreign formations in internal organs, such as stones and growths of any size. It is possible to withdraw from a body foreign objects which accidently were introduced into the body. It is also possible to provide local therapeutic treatment in the interior organs, by administering corresponding medications.

It will be understood that each of the elements described above, or two or more together, may also find a useful application in other types of constructions differing from the types described above.

While the invention has been illustrated and described as embodied in method of and device for destroying foreign formations in a body, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:

1. A device for destroying formations in a body, comprising a tubular member having an axis and introducible into a body to an area of a formation, said tubular member having a front end; gripping means provided at said front end of said tubular member for gripping a formation, said gripping means including a plurality of gripping elements which arranged around said axis in a circumferential direction and are movable between a closed position in which they are arranged without gaps between each other to form a closed space and an open position in which they are spaced from each other; a tube having a smaller diameter than a diameter or said tubular member and extending along said axis inside said tubular member, said tube having a front end connected with said gripping elements of said gripping means, said tube being axially movable inside said tubular member between one position in which it acts on said gripping elements so as to move said gripping elements to said open position and another position in which said tube acts on said gripping elements so as to move said gripping elements to said closed position; and a formation destroying element extending inside said tube and also inside the tubular member and having a front end provided with a working part operative for destroying the formation when said working part is brought in contact with the formation, so that said tube first moves said gripping elements to said open position and said gripping elements surround a formation, and then said tube moves said gripping elements to said closed position and said gripping elements are closed without gaps therebetween to form said closed space, and said formation destroying element is activated so that said working part destroys the formation, the device can be withdrawn from a body with fragments of the formation held inside said closed space formed by said gripping elements in said closed position.

2. A device as defined in claim 1, wherein said formation destroying element includes a rod which extends inside said tube and has a front end provided with said working part.

3. A device as defined in claim 1, wherein said gripping elements are formed as hinge elements.

4. A device as defined in claim 1, wherein said gripping elements are formed as springy tongues.

5. A device as defined in claim 1, and further comprising means for illuminating an area of the formation and including an eye piece for a medical practitioner, and a light guide extending from said eye piece through said tubular member.

6. A device as defined in claim 1; and further comprising a cock means for displacing said tube so as to move said gripping elements to said closed position and to said open position.

7. A device as defined in claim 1; and further comprising a handle adapted to be held by a user; and a hollow hose extending through said handle for power supply to a light source.

* * * * *